United States Patent [19]
Pannu

[11] Patent Number: 4,542,541
[45] Date of Patent: * Sep. 24, 1985

[54] UNIVERSAL INTRAOCULAR LENS

[76] Inventor: Jaswant S. Pannu, 4850 W. Oakland Park Blvd., Lauderdale Lakes, Fla. 33313

[ * ] Notice: The portion of the term of this patent subsequent to Mar. 13, 2001 has been disclaimed.

[21] Appl. No.: 425,238

[22] Filed: Sep. 28, 1982

Related U.S. Application Data

[63] Continuation-in-part of Ser. No. 329,660, Dec. 11, 1981, abandoned.

[51] Int. Cl.³ .......................... A61F 1/16; A61F 1/24
[52] U.S. Cl. ............................................... 623/6
[58] Field of Search .................................. 3/13

[56] References Cited
U.S. PATENT DOCUMENTS

| | | | |
|---|---|---|---|
| 4,159,546 | 7/1979 | Shearing | 3/13 |
| 4,249,271 | 2/1981 | Poler | 3/13 |
| 4,326,306 | 4/1982 | Poler | 3/13 |
| 4,435,855 | 3/1984 | Pannu | 3/13 |

OTHER PUBLICATIONS

American IOL International Intraocular Lenses, Style 115 Shepard Universal A/C IOL, Americn IOL International (Advertisement), Dec. 29, 1981 (1 page).
The Rayner Choyce Mark VIII Anterior Chamber Implant Catalogue No. 469, Rayner & Keeler Limited (3 pages).

Primary Examiner—Ronald L. Frinks
Attorney, Agent, or Firm—Banner, Birch, McKie & Beckett

[57] ABSTRACT

This invention resides in changing the Shearing's supporting strands on an intraocular lens which as a free-flowing pointed end is snag-prone in modifying this pointed end by reshaping it into a generally circular shaped loop wherein the end said circular shape is blunted and contiguous to the resilient strand with variations of shape in the loop including ellipsoidal, tear drop and rectangular, all of which are snag-resistant.

2 Claims, 5 Drawing Figures

UNIVERSAL INTRAOCULAR LENS

This application is a continuation in part of application Ser. No. 329,660 filed on Dec. 11, 1981, now abandoned.

BACKGROUND OF THE INVENTION

This invention resides in the structure of an intraocular lens which is implanted in an eye from which extraction has been made of a cataractous lens. The field of intraocular lens implants is a highly developed, sophisicated, medical technology. These prosthetic, or artificial, lenses are implanted following cataract surgery in either the anterior chamber or the posterior chamber of the eye. Because of the very small spaces involved, and the very delicate nature of the eye tissue, the surgery must be precise and the lens implant must be readily insertable as well as both safe and effective. Ever since the first intraocular lens was implanted, opthamologists have been searching for a universal lens, one that not only could be used for intracapsular and extracapsular implantation in either the anterior or posterior chamber of an eye but could also fit into any sized eye chamber. The lens of this invention fulfills all of these requirements.

The most commercially used intraocular lens is the Shearing Lens (U.S. Pat. No. 4,159,546) which is described for use in a posterior chamber of an eye. This lens is supported in the eye chamber by two opposed filamentous strands with one end connected to the body of the lens and the other end being free-floating and pointed resulting in a snag-prone support. The patent to Shearing is representative of the first generation technology of intraocular lens which neither required suturing nor clipping to part of the eye structure. This lens is also designed to be inserted in the posterior chamber of the eye and is generally supported by the rear wall, or posterior capsule, of the posterior chamber. The universal intraocular lens of the present invention, unlike the lens of Shearing, is designed to be functional and effective in either the anterior or the posterior chamber. The Shearing lens uses a haptic loop or flexible strand which includes a substantially straight leg portion extending away from the lens body and a curved or arch portion. The strands terminate in a free end. Shearing states that the free end is directed back toward the lens body to prevent the strand end from being pointed or jabbed against the delicate tissue within the eye during and after implantation. Thus, Shearing recognizes that damage to the eye tissue from the free end of the supporting strand of the lens can occur. The possibility of eye damage from the free end of the supporting strand with lenses, such as that of Shearing is enhanced by the surgical technique, known generally as "dialing," by which these lenses must be inserted. This requires that the lens to be rotated as it is inserted and significantly increases the risk that the free end of the flexible strand will catch on and damage eye tissue.

The applicant, who is an eye surgeon, is one of several thousands of surgeons who has been using this Shearing Lens implant. He has found that implanting this lens requires a great deal of training to implant the superior free pointed arched strand without injury to eye tissue. Proper centration often requires movement of the supporting strand which inevitably causes injury to eye tissue. A left-handed surgeon or a novitiate requires more movement for centration resulting in eye tissue injury. Knowing of these difficulties associated with implanting a Shearing Lens, applicant experimented to eliminate the free-flowing snag-prone point of the Shearing retaining filament supports. Blunting the point was not the solution. Applicant tried to use three or four retaining filaments but surprisingly found that the use of only two filaments with the point continued to form a substantially closed loop when molding it in one piece of polymethylmethacrylate would overcome the difficulties faced when using the Shearing Lens. Closing the loop resulted in a snag-free lens which upon implantation, inherently centers while the filamentous supports can then adjust to fit any sized eye chamber.

This application is filed to include the feature that the loop being formed does not have to be closed integrally with the strand. So long as the loop is formed it may end at the strand and not be integral therewith. This modification occurred during manufacture because it reduces the cost of manufacture but also provides the snag resistant feature. The present invention is directed to a one-piece intraocular lens which can be implanted in either the anterior or the posterior chambers of the eye. The lens body is supported by at least two flexible positioning and supporting elements which are integrally formed with the lens body and extended from the periphery of the lens body. The supporting elements of the invention define a continuous curved arc having a diameter of curvature greater than the diameter of the lens body. The arc is curved toward the lens surface. Snag-resistant means are integrally formed on the free end of the flexible supporting and positioning elements. In one form of the invention, the snag-resistant means is turned toward the supporting elements and terminates adjacent to, but spaced from, the elements. In another form of the invention the snag-resistant means comprises two bent arms, with one arm bent towards the lens circumference, while the second arm is bent away from the lens circumference. The two arms terminate adjacent to one another at a position opposite from the free end of the supporting elements. The present invention overcomes any danger of the free end of an intraocular lens causing damage to the eye tissue by the use of snag-resistant means on the free end of the flexible positioning and supporting strands of the lens. These snag-resistant supports at the end of the haptic loops or supporting strands reduce any possibility of hooking the iris when the lens is inserted in the posterior chamber. Additionally, due to the unique positioning of the haptic loops which define a continuous, curved arc having a diameter greater than the diameter of the lens body, the lens need not be dialed into place when inserted in the posterior chamber.

OBJECTS OF THIS INVENTION

It is the object of this invention to provide an intraocular lens having supports that are snag resistant.

It is a further object of this invention to provide an intraocular lens which can be used for implantation in either an anterior chamber or a posterior chamber.

It is a further object of this invention to provide an intraocular lens which will fit into any size of eye chamber.

Another object of this invention is to provide a lens with retaining strands that are usually properly centered upon implantation.

As a final object, there is provided a universal intraocular lens which can be used as a primary or secondary implant.

These features of this intraocular lens as well as its manner of use will be more fully explained in the following detailed disclosure along with the accompanying drawings.

BRIEF DESCRIPTION OF THE DRAWINGS

In FIG. 1, there is shown the preferred intraocular lens of this invention having its filamentous thin support members connected at one end to the body of the lens and at its other end 2 shaped into a snag-free generally circular shape. It is noted that the loop end is blunted and extends to the supporting strand but is not integral with it. The optical lens is about 6 mm and the loops about 2.5 mm each. It has been found in manufacture that it is more economical to mold the lens and its supports to provide a small opening between the strand and the loop. This modification does not affect the ability of the lens as being snag-resistant. Since the industry has shown ready acceptance of the snag-resistant lens of this invention, it is important for the applicant to cover all forms of snag-resistant lenses to adapt to manufacturing needs and to protect variants of this lens.

An intraocular lens of the present invention includes a lens body 1 and at least two spaced flexible positioning and supporting elements or haptics integrally formed with lens body 1 as a one-piece construction and extending radially outwardly from the periphery of lens body 1. The haptics define a continuous, curved arc having a diameter greater than the diameter of lens body 1. The arc of the haptics is curved toward the lens circumference and terminates in a free end spaced from the lens periphery. Snag-resistant means or loops 2 are integrally formed on the free end of the haptics for smoothly guiding and positioning the lens across eye tissue when implanting the lens. Snag-resistant means 2 extend from the free end of the haptics and turn inwardly toward the haptics. Snag-resistent means 2 have an outer end which terminates adjacent to but spaced from the haptics. Loops 2 are substantially greater in size or diameter than the width of the haptics. In FIGS. 2, 4 and 5, the snag-resistant means are shown in various shapes at 3, 5 and 8, respectively.

In FIG. 3, another embodiment is shown in which the snag-resistant means have a first arm 4 bent towards the lens circumference and a second arm 6 bent away from the lens circumference. The first and second arms terminating in an adjacent, spaced configuration at a position opposite from the free end of the haptics.

In FIG. 2, there is shown a snag-resistant intraocular lens having a tear drop shape 3. In FIG. 3, there is shown a similar lens having a rectangular shape with its non joinder at 6 whereas FIG. 4 shows the same lens as FIG. 3 with its non joinder at 7. In FIG. 5, there is shown the same lens as in FIG. 4 except that the shape of the loop is elliptical and its non-joinder area is at 8.

Figure 1:
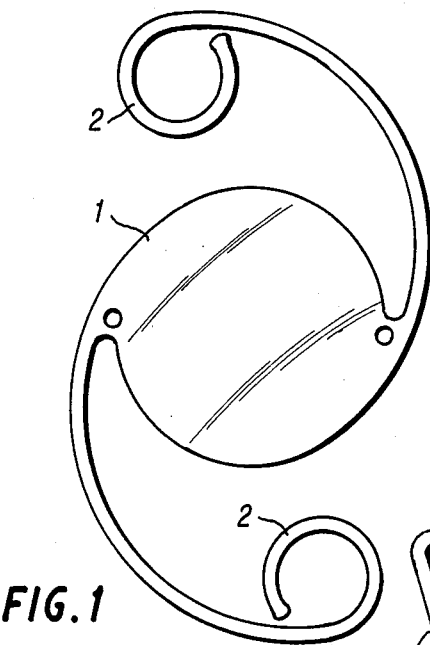
FIG. 1 is a front schematic elevational view wherein the filamentous supporting strand ends in a loop which is approximately circular.
Figure 2:
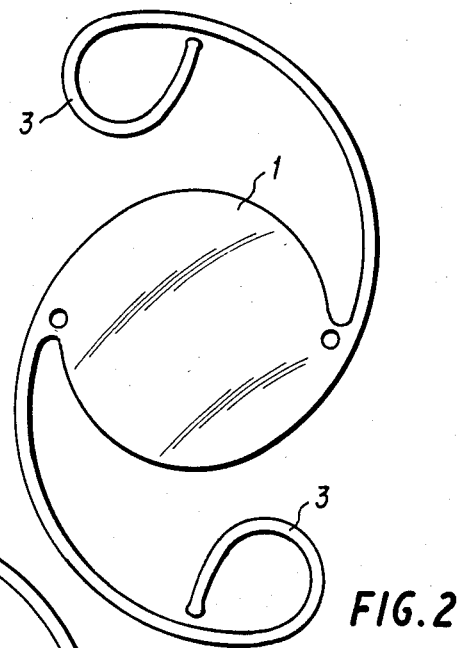
FIG. 2 is the same as FIG. 1 except that the loop is tear drop shape.
Figure 3:
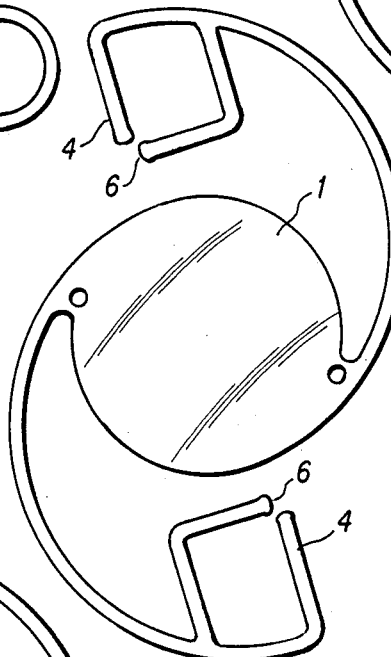
FIG. 3 is the same as FIG. 1 except that the loop is rectangular shaped.
Figure 4:
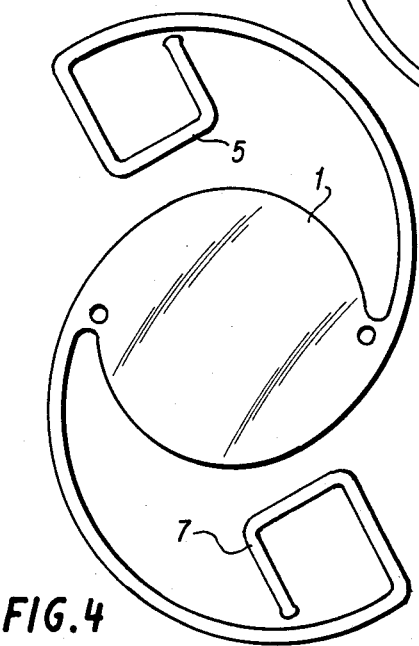
FIG. 4 is the same as FIG. 3 except for the contiguous opening being in a different location.
Figure 5:
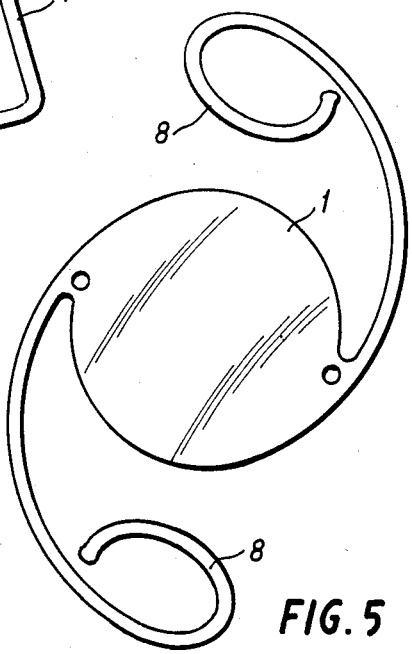
FIG. 5 is the same as FIG. 1 except that the loop is shaped as an ellipse.

The lens of this invention could be composed of polymethylmethacrylate, polypropylene, nylon and other polyamides. In addition, the lens may be plano-convex, concavo, convex or bi-convex. In addition the lens can be slightly tinted.

In conclusion, the following beneficial effects are obtained by the use of the intraocular lens of this invention:

1. There is no pointed free-end of the supporting filament that can get entangled in the eye tissue.

2. Endothelial damage to the cornea of the eye is avoided because the lens of this invention is usually self-centering upon implantation.

3. No sunset syndrome can occur and no change to break zonules during inplantation.

4. Can guess the size of the ciliary sulcus by observing the distance between the optical portion of the lens and the loop.

5. Surgeons can easily learn the implantation process because it can be done with one hand. Third World potential is increased because of ease of implantation with almost automatic centration in the Third World having less skilled surgeons.

6. Surgeons are provided with a universal lens which can be equally used in a posterior or anterior chamber or in any size of chamber. This eliminates stocking by surgeons of three different sizes of lenses.

Those skilled in the art will also appreciate that there are various modifications of the precise form of the pseudophakis shown and described in this specification. Accordingly, the foregoing illustrations are not to be interpreted as restrictive beyond that necessitated by the following claims:

What is claimed is:

1. An intraocular lens comprising:

a lens body;

at least two spaced flexible positioning and supporting elements integrally formed with said lens body as a one-piece construction and extending radially outwardly from the periphery of said lens body;

said elements defining a continuous, curved arc having a diameter greater than the diameter of said lens body, said arc curved toward said lens circumference and terminating in a free end spaced from said periphery; and snag-resistant means integrally formed on the free end of said elements for smoothly guiding and positioning the lens across eye tissue when implanting the lens, said snag-resistant means extending from said free end, turned towards said elements, and having an outer periphery which terminates adjacent to but spaced from said flexible elements and is substantially greater in size than the width of said flexible elements.

2. An intraocular lens comprising:

a lens body;

at least two spaced flexible positioning and supporting elements integrally formed with said lens body as a one-piece construction and extending radially outwardly from the periphery of said lens body;

said elements defining a continuous, curved arc having a diameter greater than the diameter of said lens body, said arc curved toward said lens circumference and terminating in a free end spaced from said periphery; and snag-resistant means integrally formed on the free end of said elements for smoothly guiding and positioning the lens across eye tissue when implanting the lens, said snag-resistant means having a first arm bent towards said lens circumference and a second arm bent away from said lens circumference, said first and second arms terminating in an adjacent, spaced configuration at a position opposite from said free end.

* * * * *